(12) United States Patent
Fitzsimmons

(10) Patent No.: US 9,982,246 B2
(45) Date of Patent: May 29, 2018

(54) FLUID DELIVERY SYSTEMS INCLUDING HYDRAULIC DRIVE SYSTEMS

(71) Applicant: FITZSIMMONS HYDRAULICS, INC., Clarence, NY (US)

(72) Inventor: Michael M. Fitzsimmons, Naples, FL (US)

(73) Assignee: FITZSIMMONS HYDRAULICS, INC., Clarence, NY (US)

( * ) Notice: Subject to any disclaimer, the term of this patent is extended or adjusted under 35 U.S.C. 154(b) by 0 days. days.

(21) Appl. No.: 15/234,381

(22) Filed: Aug. 11, 2016

(65) Prior Publication Data

US 2018/0045226 A1 Feb. 15, 2018

(51) Int. Cl.
*F15B 21/04* (2006.01)
*C12N 9/22* (2006.01)
*C12N 15/90* (2006.01)

(52) U.S. Cl.
CPC ............. *C12N 9/22* (2013.01); *C12N 15/907* (2013.01); *C07K 2319/00* (2013.01); *C07K 2319/80* (2013.01)

(58) Field of Classification Search
CPC .......... F15B 1/26; F15B 7/005; F15B 21/042; F15B 2211/20546
See application file for complete search history.

(56) References Cited

U.S. PATENT DOCUMENTS

| 4,738,115 A * | 4/1988 | Goode | F17C 9/02 60/618 |
|---|---|---|---|
| 5,222,875 A | 6/1993 | Clark | |
| 8,104,947 B2 * | 1/2012 | Ando | B28C 5/4213 366/54 |
| 2001/0032618 A1 * | 10/2001 | Ramseyer | F02M 59/06 123/446 |
| 2009/0064675 A1 * | 3/2009 | Dvorak | F16H 61/4017 60/464 |

* cited by examiner

*Primary Examiner* — F. Daniel Lopez
*Assistant Examiner* — Abiy Teka
(74) *Attorney, Agent, or Firm* — Jones Robb, PLLC

(57) ABSTRACT

A hydraulic drive system includes a unidirectional pump, a charge pump configured to supply an input of the unidirectional pump with a hydraulic fluid pressurized with a charge pressure, a hydraulic motor, and a flow control valve configured to meter a flow of hydraulic fluid from an output of the unidirectional pump to a fluid input of the hydraulic motor. The hydraulic motor comprises a fluid output configured to be in direct fluid communication with the input of the unidirectional pump. Fluid delivery systems include hydraulic drive systems.

16 Claims, 3 Drawing Sheets

FLUID DELIVERY SYSTEMS INCLUDING HYDRAULIC DRIVE SYSTEMS

TECHNICAL FIELD

The present disclosure relates generally to hydraulic drive systems used in fluid delivery systems.

BACKGROUND

Delivery of commercial fluids from fluid transportation vehicles is conventionally accomplished with hydraulic drive systems that include a hydraulic pump driven by a prime mover (e.g., an internal combustion engine) of the delivery vehicle, a hydraulic motor driven by the hydraulic pump, and a fluid delivery pump mechanically coupled to and driven by the hydraulic motor. The hydraulic pump converts torque from the prime mover into a flow of pressurized working fluid (e.g., hydraulic fluid), which is used to drive the hydraulic motor. Torque generated by the hydraulic motor in response to the flow of pressurized hydraulic fluid delivered by the hydraulic pump rotates the fluid delivery pump, which offloads the commercial fluid from the vehicle.

The hydraulic pump and hydraulic motor may be located remote from one another and may be connected through fluid lines. For example, the hydraulic pump may be located on a tractor portion of a tractor-trailer and driven by a power take-off (PTO) of the tractor's drivetrain, while the hydraulic motor and fluid delivery pump may be located on the trailer portion. Such drive systems may include various other hydraulic componentry such as control valves, fluid reservoirs, fluid coolers, etc.

A need exists to improve such fluid delivery systems. For example, it is desirable to reduce weight and complexity of such fluid delivery systems and the associated hydraulic drive systems.

SUMMARY

In accordance with various exemplary embodiments, a hydraulic drive system includes a unidirectional pump, a charge pump configured to supply an input of the unidirectional pump with a hydraulic fluid pressurized with a charge pressure, a hydraulic motor; and a flow control valve configured to meter a flow of hydraulic fluid from an output of the unidirectional pump to a fluid input of the hydraulic motor. The hydraulic motor comprises a fluid output configured to be in direct fluid communication with the input of the unidirectional pump.

In accordance with various exemplary embodiments, a fluid delivery system includes a closed-loop hydraulic drive system. The closed-loop hydraulic drive system includes a unidirectional hydraulic pump configured to be driven by a power take off of a vehicle, a hydraulic motor configured to be driven by the unidirectional hydraulic pump, and a fluid delivery pump coupled with an output shaft of the hydraulic motor.

The accompanying drawings, which are incorporated in and constitute a part of this specification, illustrate embodiments of the present disclosure and together with the description, serve to explain the principles of the present disclosure.

BRIEF DESCRIPTION OF THE DRAWINGS

At least some features and advantages will be apparent from the following detailed description of embodiments consistent therewith, which description should be considered with reference to the accompanying drawings, wherein.

Figure 1:
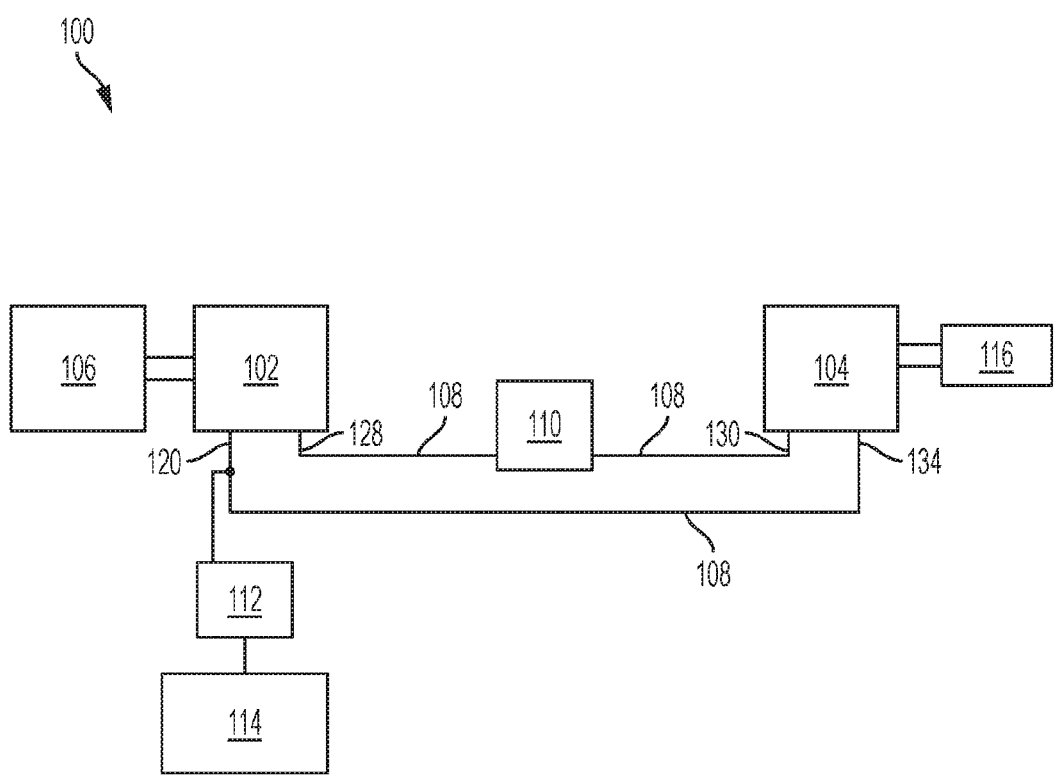
FIG. 1 is a schematic representation of a fluid delivery system including a hydraulic drive system according to an exemplary embodiment of the disclosure.

Although the following detailed description makes reference to illustrative embodiments, many alternatives, modifications, and variations thereof will be apparent to those skilled in the art. Accordingly, it is intended that the claimed subject matter be viewed broadly.

DESCRIPTION OF THE EMBODIMENTS

Reference will now be made in detail to various embodiments, examples of which are illustrated in the accompanying drawings. However, these various exemplary embodiments are not intended to limit the disclosure. To the contrary, the disclosure is intended to cover alternatives, modifications, and equivalents. In the drawings and the description, similar elements are provided with similar reference numerals. The features explained individually in the description can be mutually combined in any technically expedient manner and disclose additional embodiments of the present disclosure.

The present disclosure relates to hydraulic drive systems, and fluid delivery systems including such hydraulic drive systems, configured for reduced weight and reduced complexity compared to conventional hydraulic drive systems utilized with fluid delivery systems. Exemplary embodiments of the disclosure include closed-loop hydraulic systems utilizing a unidirectional hydraulic pump to drive a hydraulic motor. The hydraulic motor is mechanically coupled with a pump, such as a fluid delivery pump of a fluid transport vehicle, and the unidirectional hydraulic pump may be mechanically coupled with a drivetrain of the fluid transport vehicle. For example, the unidirectional hydraulic pump may be mechanically coupled with a power take-off (PTO) of the fluid transport vehicle. In exemplary embodiments, the hydraulic drive system of the fluid delivery system may include a charge pump configured to pressurize a fluid inlet of the unidirectional hydraulic pump. In exemplary embodiments, the charge pressure is equal to or less than about 100 pounds per square inch (psi). For example, the charge pressure may be equal to about 50 psi.

In exemplary embodiments, the charge pump comprises a gear pump mechanically driven in conjunction with (e.g., connected to a common PTO, gearbox, etc.) the unidirectional hydraulic pump. The unidirectional hydraulic pump may comprise an axial piston pump with a fixed thrust plate or a variable angle swashplate, or may comprise another type of positive-displacement pump configured to generate a flow of hydraulic fluid in a single direction for a given direction of rotation. In exemplary embodiments, the closed-loop hydraulic drive system includes a fluid reservoir from which the charge pump may draw hydraulic fluid. One or more relief valves are configured to divert a portion of a fluid flow to the reservoir, and may be configured to prevent over-pressurization in the charge pump, unidirectional pump, the hydraulic motor, or other components of the hydraulic drive system.

The hydraulic drive system may further comprise a control valve configured to regulate (e.g., control, meter, etc.) a flow of hydraulic fluid from the unidirectional hydraulic pump. In an exemplary embodiment, the control valve is a proportional valve. In some exemplary embodiments, the control valve may be manually operated, or may include electronic or other automated controls.

Referring now to FIG. 1, an exemplary embodiment of a simplified fluid delivery system 100 according to the disclosure is shown. The fluid delivery system 100 of FIG. 1 includes a unidirectional hydraulic pump 102 fluidly coupled to a hydraulic motor 104 in a closed-loop configuration. The unidirectional hydraulic pump 102 is mechanically coupled to a drivetrain 106 of, e.g., a fluid delivery vehicle (not shown). The drivetrain 106 may be or include an internal combustion engine, such as a diesel or gasoline engine, a transmission, and/or other drivetrain components. In an exemplary embodiment, the unidirectional hydraulic pump 102 is coupled to the drivetrain 106 through a power take-off (PTO), such as a clutch-dependent power take-off configured to be driven by a layshaft of a gearbox of the drivetrain 106. Other configurations and devices for coupling the unidirectional hydraulic pump 102 and the drivetrain 106, such as clutch-independent power take-offs, or other arrangements, are within the scope of the disclosure.

The unidirectional hydraulic pump 102 and the hydraulic motor 104 are in fluid communication through fluid lines 108. A control valve 110 is located between an outlet 128 of the unidirectional hydraulic pump 102 and an inlet 130 of the hydraulic motor 104 and controls (e.g., meters) a flow of hydraulic fluid through the fluid line 108 connecting the outlet 128 of the unidirectional hydraulic pump 102 and the inlet 130 of the hydraulic motor 104. In an exemplary embodiment, the control valve 110 comprises a proportional control valve. The control valve 110 may be manually operated, may include an automated or partially automated electronic control system, or other features.

The fluid delivery system 100 includes a charge pump 112 configured to supply a flow of pressurized hydraulic fluid to an inlet 120 of the unidirectional hydraulic pump 102, as discussed in greater detail below in connection with FIG. 2. The charge pump 112 is configured to draw a supply of hydraulic fluid from a fluid reservoir 114, which may be, e.g., a cyclonic reservoir or other reservoir. The hydraulic fluid may flow into the reservoir 114 from one or more pressure relief valves (e.g., pressure relief valve 222 shown in FIG. 2) associated with the charge pump 112, the control valve 110, from drains (e.g., drain 232 of the hydraulic motor 204 shown in FIG. 2) on the unidirectional hydraulic pump 102 and hydraulic motor 104, and/or other components.

The hydraulic motor 104 is mechanically coupled with a fluid delivery pump 116. In an exemplary embodiment, the fluid delivery pump 116 is configured to offload a fluid (e.g., commercial bulk fluid) transported by the fluid delivery vehicle. The mechanical coupling between the hydraulic motor 104 and the fluid delivery pump 116 may comprise a drive coupling such as, e.g., a Lovejoy splined coupling, a clutched interface, etc. In one exemplary embodiment, the fluid delivery pump 116 comprises a pump configured to offload a cryogenic fluid from the fluid delivery vehicle.

In operation, a torque supplied by the drivetrain 106 drives the unidirectional hydraulic pump 102, generating pressure in the hydraulic fluid flowing from the outlet 128 of the unidirectional hydraulic pump 102. The pressurized hydraulic fluid flows through the lines 108 at a flow rate determined by a position of the control valve 110. The pressurized hydraulic fluid enters the inlet 130 of the hydraulic motor 104, causing rotation of the hydraulic motor 104 and the fluid delivery pump 116, resulting in offloading of the commercial fluid from the fluid delivery vehicle. Hydraulic fluid exiting an outlet 134 of the hydraulic motor 104 is directed through lines 108 back to the inlet 120 of the unidirectional hydraulic pump 102.

As the hydraulic fluid flows through the unidirectional hydraulic pump 102 and the hydraulic motor 104, intentional clearances and/or required manufacturing tolerances of internal components of the unidirectional hydraulic pump 102 and/or hydraulic motor 104 may permit a portion of the hydraulic fluid to leak from the main circuit (e.g., a circuit comprising the unidirectional hydraulic pump 102, the control valve 110, and the hydraulic motor 104). Such fluid leakage is directed through drains of the respective components (as discussed and shown in FIG. 2) to the reservoir 114, where it accumulates. The charge pump 112 is configured to draw a supply of hydraulic fluid from the reservoir 114, pressurize the hydraulic fluid, and deliver the pressurized hydraulic fluid to the inlet 120 of the unidirectional hydraulic pump 102 to replace the fluid lost through the drains of the unidirectional hydraulic pump 102 and hydraulic motor 104.

Figure 2:
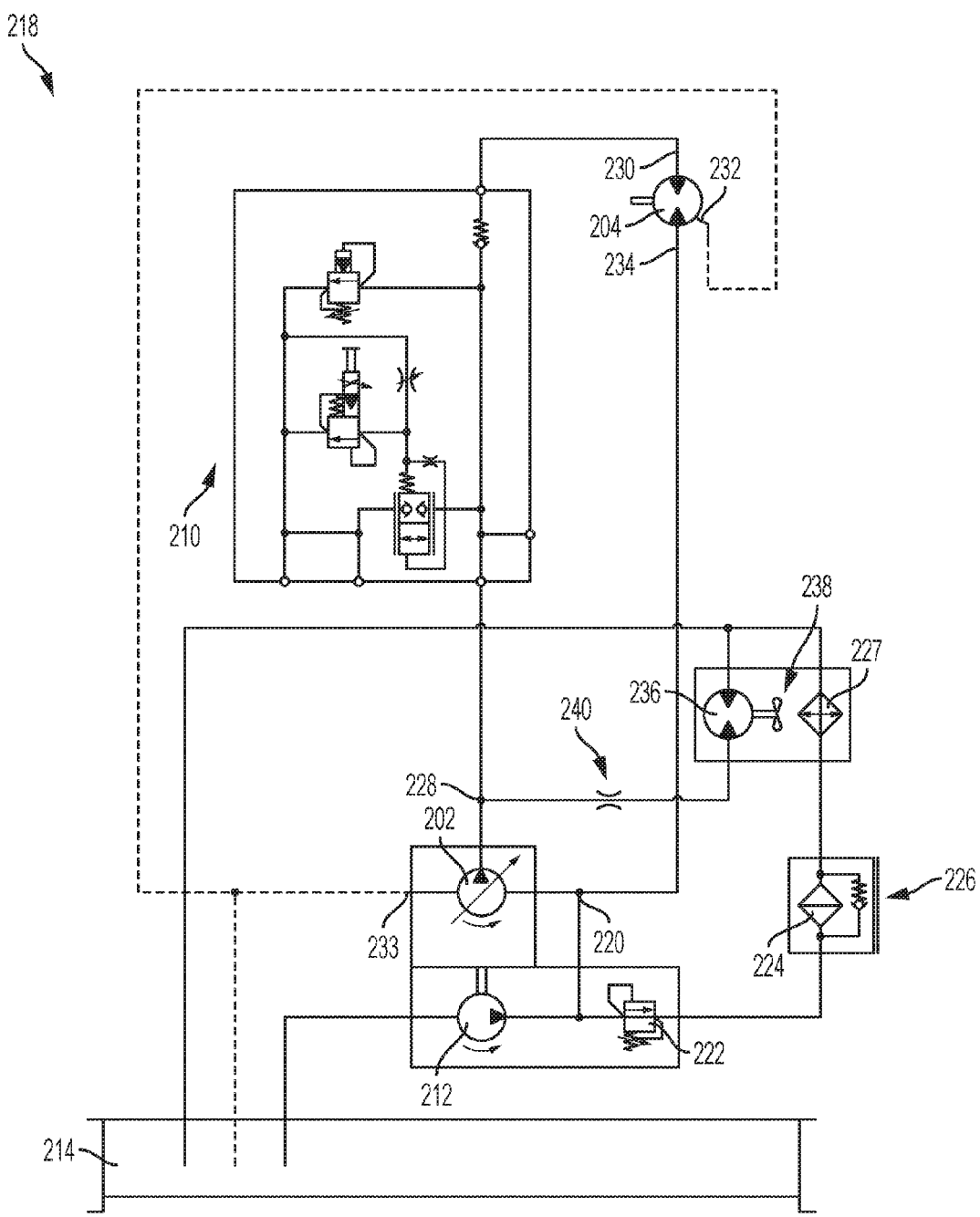
FIG. 2 is a schematic diagram of a hydraulic drive system according to an exemplary embodiment of the disclosure.

Referring now to FIG. 2, a schematic representation of a hydraulic drive system 218 is shown. The hydraulic drive system 218 includes a unidirectional hydraulic pump 202. As noted above, the unidirectional hydraulic pump 202 may be or include an axial piston pump with a fixed thrust plate or a variable angle swash plate. In embodiments with a variable angle swashplate, the swashplate may be variable only in one rotational direction from a neutral position (i.e., a position in which the swashplate is oriented perpendicular to a rotational driveshaft of the pump) as discussed in connection with FIG. 3 below. This is in contrast to a conventional overcenter pump, in which a variable swashplate is variable in two directions from a neutral position to provide two selectable flow directions for a rotational input applied to a driveshaft of the pump in a single direction.

The hydraulic drive system 218 includes a charge pump 212 configured to draw hydraulic fluid from a reservoir 214 and deliver a flow of pressurized hydraulic fluid to an inlet 220 of the unidirectional hydraulic pump 202. The charge pump 212 may be a gear pump or another configuration of positive-displacement pump driven by the same mechanical drive as the unidirectional hydraulic pump 202. For example, the charge pump 212 may be driven from the same power take-off as the unidirectional hydraulic pump 202, e.g., as described above in connection with FIG. 1. In an exemplary embodiment, an input shaft of the charge pump 212 may be mechanically coupled with an input shaft of the unidirectional hydraulic pump 202. A housing of the charge pump 212 may be coupled with or integral with a housing of the unidirectional hydraulic pump 202.

In comparison to the requirements of overcenter pumps conventionally used in closed-loop hydraulic drive systems, the pressure required to be supplied by the charge pump 212 to the inlet 220 of the unidirectional hydraulic pump 202 may be significantly lower. For example, conventional overcenter hydraulic pumps employed in a closed-loop hydraulic drive system may require at least about 300 to 400 psi of pressure to prevent cavitation of the hydraulic fluid and resulting damage to components of the hydraulic drive system. In addition, high charge pressures may be required in conventional overcenter hydraulic pumps to shift servos linked to an adjustable swash plate configured to allow pumping the hydraulic fluid in two selectable directions. In addition, a conventional overcenter pump may require a charge pressure at two separate inlet ports. All of these factors may contribute to a requirement for a high charge pressure (e.g., equal to or greater than about 300 psi) for proper functioning of the system.

In exemplary embodiments of the disclosure, the charge pump 212 is configured to deliver hydraulic fluid to the inlet 220 of the unidirectional hydraulic pump 202 at pressures of, for example, less than about 100 psi (689 kPa). For example, the charge pump 212 is configured to deliver hydraulic fluid to the inlet 220 of the unidirectional hydraulic pump 202 at a pressure of about 50 psi (344 kPa) or less. As the unidirectional hydraulic pump 202 does not include internal servo valves and does not require pressurization of multiple inlets, the charge pressure provided to the unidirectional hydraulic pump 202 can be significantly lower than that provided to a conventional overcenter pump in a comparable system. Such a reduction in charge pressure compared to conventional systems enables use a smaller, lighter charge pumps, and results in less torque being drawn from the power take-off or other drive. In addition, a lower charge pressure results in less heat being added to the system, and thereby may enable use of smaller cooling components and contribute to improved reliability of the system.

In the exemplary embodiment of FIG. 2, a portion of the flow of pressurized hydraulic fluid from the charge pump 212 is diverted through a relief valve 222, where it enters a fluid filter 224 configured to remove contaminates, such as particulate foreign material, from the hydraulic fluid. A check valve 226 is configured to enable the flow of fluid to bypass the filter 224 if the filter 224 becomes clogged with foreign matter or becomes otherwise inoperable. The filter 224 may comprise any suitable filtration media, such as glass fibers, cellulose fibers, polymer fibers, etc.

In some exemplary embodiments, an outlet flow of hydraulic fluid from the filter 224 is directed to a heat exchanger 227 configured to transfer heat from the hydraulic fluid to another medium, such as atmospheric air. For example, the heat exchanger 227 may comprise a stacked-plate heat exchanger, a coil and tube heat exchanger, etc. An outlet flow of filtered, cooled hydraulic fluid from the filter 224 and heat exchanger 227 is directed to the reservoir 214.

Pressurized hydraulic fluid from an outlet 228 of the unidirectional hydraulic pump 202 is directed (e.g., through fluid lines 108 shown in FIG. 1) to a control valve 210, which, as described above, may be a proportional valve with electronic control.

A metered flow of pressurized hydraulic fluid from the control valve 210 enters a fluid inlet 230 of a hydraulic motor 204, driving rotation of the hydraulic motor 204 and a fluid delivery pump (e.g., fluid delivery pump 116 shown in FIG. 1) to which the hydraulic motor 204 is coupled by a mechanical coupling. A portion of the hydraulic fluid flowing through the hydraulic motor 204 may leak through clearances between internal components in the hydraulic motor 204 and exit the motor 204 through the drain 232 and flow to the reservoir 214. The remainder of the fluid flow through the motor 204 exits an outlet 234 of the hydraulic motor 204.

The outlet 234 of the hydraulic motor 204 is directly connected (e.g., through a fluid line such as fluid lines 118 shown in FIG. 1) to the inlet 220 of the unidirectional hydraulic pump 202. Stated another way, the outlet 234 of the hydraulic motor 204 is in direct fluid communication (i.e., in a closed loop) with the inlet 220 of the unidirectional hydraulic pump 202. This is in contrast to an open-loop system, in which a flow of fluid exiting a motor is directed entirely to a fluid reservoir, and the inlet of a pump draws hydraulic fluid from the reservoir, rather than accepting a flow directly from the outlet of a hydraulic motor. The flow from the outlet 234 of the hydraulic motor 204 is combined with the outlet of the charge pump 212, and the combined flow enters the inlet 220 of the unidirectional hydraulic pump 202. As with the hydraulic motor 204, clearances within the unidirectional hydraulic pump 202 may allow a portion of the hydraulic fluid flowing through the unidirectional hydraulic pump 202 to leak between components of the unidirectional hydraulic pump 202 and flow through a drain 233 and into the fluid reservoir 214.

According to an exemplary embodiment, a portion of the fluid flow from the outlet 228 of the unidirectional hydraulic pump 202 is diverted to a secondary hydraulic motor 236 mechanically coupled with a fan or blower 238 configured to generate airflow through the heat exchanger 226. The flow of fluid through the secondary hydraulic motor 236 is metered by a secondary control valve 240, which may be physically integrated with the control valve 210, or may be a separate component. Control of the secondary control valve 240 may be based on a temperature of the fluid, a flowrate through the hydraulic motor 204, or other operating conditions of the hydraulic drive system.

Figure 3:
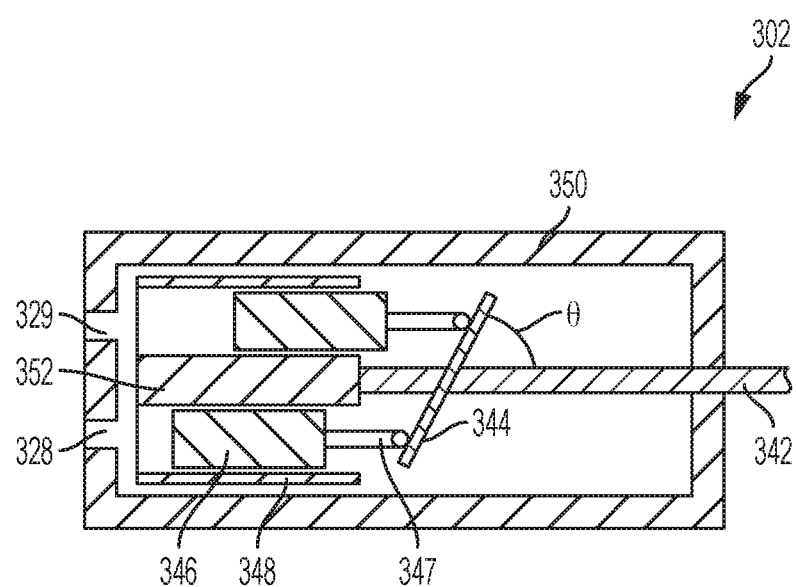
FIG. 3 is a simplified cross-sectional view of an axial piston pump according to an exemplary embodiment of the disclosure.

Referring now to FIG. 3, a unidirectional hydraulic pump 302 is shown in simplified cross section. The unidirectional hydraulic pump 302 includes a drive shaft 342 configured to be driven (e.g., rotated) by a PTO or other rotating drive as described above. A fixed-angle thrust plate 344 is stationary with a body 350 of the unidirectional hydraulic pump 302, and is oriented at an angle θ relative to the rotating drive shaft 342. A plurality of pistons 346 are disposed within a respective plurality of cylinders 348 formed in a cylinder block 352. The cylinder block 352 and pistons 346 rotate as an assembly with the drive shaft 342. A plurality of connecting rods 347 associated respectively with each piston of the plurality of pistons 346 are constrained to follow the thrust plate 344 as the drive shaft 342 rotates. The plurality of pistons 346 reciprocate within the respective plurality of cylinders 348 as the drive shaft 342 rotates and create pumping action to draw hydraulic fluid in through an inlet 320 and subsequently force the hydraulic fluid out through an outlet 328.

As described above, in an exemplary embodiment, the angle θ of the thrust plate 344 is fixed with respect to the drive shaft 342. In other embodiments, the angle θ is adjustable between a neutral position (i.e., a position at which the angle θ is equal to 90 degrees and rotation of the drive shaft 342 does not cause any reciprocating motion of the pistons 346) and a position in which the angle is less than 90 degrees and greater than 0 degrees. In contrast, in an overcenter pump, the angle θ is variable between angles less than and greater than 90 degrees (i.e., the angle θ can be varied in two directions from the neutral position).

Hydraulic drive systems according to exemplary embodiments of the disclosure may exhibit less weight, better efficiency, and lower operating temperatures than conventional closed-loop systems employing overcenter hydraulic pumps. For example, the lower required charge pressure of the hydraulic drive systems of the disclosure results in less energy wasted as heat added to the hydraulic fluid. In addition, hydraulic drive systems of the present disclosure may include fewer component parts than and exhibit improved reliability compared to a conventional closed-loop hydraulic drive system using an overcenter pump.

Further modifications and alternative embodiments will be apparent to those of ordinary skill in the art in view of the disclosure herein. For example, systems may include additional components or steps that were omitted from the diagrams and description for clarity of operation. Accordingly, this description is to be construed as illustrative only and is for the purpose of teaching those skilled in the art the general manner of carrying out the present teachings. It is to be understood that the various embodiments shown and described herein are to be taken as exemplary. Elements and materials, and arrangements of those elements and materials, may be substituted for those illustrated and described herein, parts and processes may be reversed, and certain features of the present teachings may be utilized independently, all as would be apparent to one skilled in the art after having the benefit of the description herein. Changes may be made in the elements described herein without departing from the spirit and scope of the present teachings and following claims.

This description and the accompanying drawings that illustrate exemplary embodiments of the present teachings should not be taken as limiting. Various mechanical, compositional, structural, electrical, and operational changes may be made without departing from the scope of this description and the claims, including equivalents. In some instances, well-known structures and techniques have not been shown or described in detail so as not to obscure the disclosure. Like numbers in two or more figures represent the same or similar elements. Furthermore, elements and their associated features that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment.

For the purposes of this specification and appended claims, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the written description and claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," include plural referents unless expressly and unequivocally limited to one referent. Thus, for example, reference to "a sensor" includes two or more different sensors. As used herein, the term "include" and its grammatical variants are intended to be non-limiting, such that recitation of items in a list is not to the exclusion of other like items that can be substituted or added to the listed items.

It will be apparent to those skilled in the art that various modifications and variations can be made to the systems of the present disclosure without departing from the scope of the disclosure. It is to be understood that the particular examples and embodiments set forth herein are non-limiting, and modifications to structure, dimensions, materials, and methodologies may be made without departing from the scope of the present teachings. Other embodiments of the disclosure will be apparent to those skilled in the art from consideration of the specification and practice of the disclosure disclosed herein. It is intended that the specification and embodiments described herein be considered as exemplary only.

What is claimed is:

1. A hydraulic drive system, comprising:
   a unidirectional pump;
   a charge pump configured to supply an input of the unidirectional pump with a hydraulic fluid pressurized with a charge pressure;
   a hydraulic motor with an output shaft;
   a flow control valve configured to meter a flow of hydraulic fluid from an output of the unidirectional pump to a fluid input of the hydraulic motor; and
   a fluid delivery pump mechanically coupled to the output shaft of the hydraulic motor;
   wherein the hydraulic motor comprises a fluid output configured to be in direct fluid communication with the input of the unidirectional pump.

2. The hydraulic drive system of claim 1, wherein the drive system further comprises a fluid reservoir, and wherein the charge pump is configured to draw hydraulic fluid from the fluid reservoir.

3. The hydraulic drive system of claim 2, wherein the drive system further comprises a heat exchanger configured to extract heat from the hydraulic fluid.

4. The hydraulic drive system of claim 3, wherein the heat exchanger is configured for fluid communication with the output of the unidirectional pump and the reservoir.

5. The hydraulic drive system of claim 2, wherein at least one of the charge pump, the unidirectional pump, and the hydraulic motor comprise a relief valve configured to be in fluid communication with the reservoir.

6. The hydraulic drive system of claim 1, wherein the flow control valve comprises a proportioning valve.

7. The hydraulic drive system of claim 1, wherein the unidirectional pump comprises a variable displacement pump.

8. The hydraulic drive system of claim 7, wherein the unidirectional pump comprises an axial piston pump.

9. The hydraulic drive system of claim 8, wherein the unidirectional pump comprises an axial piston pump with a fixed-angle thrust plate.

10. The hydraulic drive system of claim 1, wherein the hydraulic motor is configured to drive the fluid delivery pump to deliver a liquid.

11. The hydraulic drive system of claim 1, wherein the delivery pump comprises a cryogenic pump.

12. The hydraulic drive system of claim 1, wherein the unidirectional pump is configured to be driven by a power take-off of a drivetrain of a vehicle.

13. The hydraulic drive system of claim 1, wherein the charge pump comprises a gear pump.

14. The hydraulic drive system of claim 1, wherein the charge pressure is equal to or less than 100 pounds per square inch.

15. The hydraulic drive system of claim 14, wherein the charge pressure is equal to 50 pounds per square inch.

16. The hydraulic drive system of claim 1, wherein the hydraulic motor is directly coupled to the fluid delivery pump.

* * * * *